US00PP25325P2

(12) United States Plant Patent
Geibel

(10) Patent No.: US PP25,325 P2
(45) Date of Patent: Mar. 3, 2015

(54) ***PELARGONIUM* PLANT NAMED 'PACBLUEBE'**

(50) Latin Name: *Pelargonium crispum*
Varietal Denomination: Pacbluebe

(71) Applicant: Martin Geibel, Dresden (DE)

(72) Inventor: Martin Geibel, Dresden (DE)

(73) Assignee: Elsner Pac Jungpflanzen GbR, Dresden (DE)

( * ) Notice: Subject to any disclaimer, the term of this patent is extended or adjusted under 35 U.S.C. 154(b) by 34 days.

(21) Appl. No.: 13/986,779

(22) Filed: Jun. 4, 2013

(51) Int. Cl.
*A01H 5/00* (2006.01)

(52) U.S. Cl.
USPC ..... Plt./324

(58) Field of Classification Search
USPC ..... Plt./324
See application file for complete search history.

*Primary Examiner* — Kent L Bell
(74) *Attorney, Agent, or Firm* — C. A. Whealy

(57) ABSTRACT

A new and distinct *Pelargonium* plant named 'Pacbluebe', characterized by its upright and uniformly rounded plant habit; moderately vigorous growth habit; freely basal branching habit; early and freely flowering habit; dark and light purple bi-colored flowers that are held above the foliar plane on strong peduncles; no requirement for cooling treatment; and long flowering period.

1 Drawing Sheet

Botanical designation: *Pelargonium crispum*.
Cultivar denomination: 'PACBLUEBE'.

BACKGROUND OF THE INVENTION

The present invention relates to a new and distinct cultivar of *Pelargonium* plant, botanically known as *Pelargonium crispum*, and hereinafter referred to by the name 'Pacbluebe'.

The new *Pelargonium* plant is a product of a planned breeding program conducted by the Inventor in Dresden, Germany. The objective of the breeding program is to develop new early and freely flowering *Pelargonium* plants with attractive flowers.

The new *Pelargonium* plant originated from a cross-pollination made by the Inventor in Dresden, Germany during the summer of 2006 of two unnamed proprietary selections of *Pelargonium crispum*, not patented. The new *Pelargonium* plant was discovered and selected by the Inventor as a flowering plant from within the progeny of the stated cross-pollination in a controlled greenhouse environment in Dresden, Germany during the spring of 2007.

Asexual reproduction of the new *Pelargonium* plant by vegetative terminal cuttings in a controlled greenhouse environment in Dresden, Germany since October, 2007 has shown that the unique features of this new *Pelargonium* plant are stable and reproduced true to type in successive generations.

SUMMARY OF THE INVENTION

Plants of the new *Pelargonium* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Pacbluebe'. These characteristics in combination distinguish 'Pacbluebe' as a new and distinct *Pelargonium* plant:

1. Upright and uniformly rounded plant habit.
2. Moderately vigorous growth habit.
3. Freely basal branching habit.
4. Early and freely flowering habit.
5. Dark and light purple bi-colored flowers that are held above the foliar plane on strong peduncles.
6. Does not require cooling treatment for flower development.
7. Long flowering period.

Plants of the new *Pelargonium* differ primarily from plants of the parent selections in flower coloration. In addition, plants of the new *Pelargonium* are more uniform than plants of the parent selections.

Plants of the new *Pelargonium* can be compared to plants of the *Pelargonium crispum* 'Pacburg', disclosed in U.S. Plant Pat. No. 14,862. In side-by-side comparisons conducted in Dresden, Germany, plants of the new *Pelargonium* differed from plants of 'Pacburg' in the following characteristics:

1. Plants of the new *Pelargonium* had narrower leaves and leaf petioles than plants of 'Pacburg'.
2. Plants of the new *Pelargonium* had broader leaves than plants of 'Pacburg'.
3. Plants of the new *Pelargonium* and 'Pacburg' differed in flower color.
4. Plants of the new *Pelargonium* had longer peduncles (umbel stems) than plants of 'Pacburg'.

BRIEF DESCRIPTION OF THE PHOTOGRAPH

The accompanying colored photograph illustrates the overall appearance of the new *Pelargonium* plant showing the colors as true as it is reasonably possible to obtain in colored reproductions of this type. Colors in the photograph may differ slightly from the color values cited in the detailed botanical description which accurately describe the colors of the new *Pelargonium* plant. The photograph comprises a side perspective view of a typical flowering plant of 'Pacbluebe' grown in a container.

DETAILED BOTANICAL DESCRIPTION

The aforementioned photograph and following observations, measurements and values describe plants grown in 19-cm containers during the winter, spring and summer in a glass-covered greenhouse in Dresden, Germany and under cultural practices typical of commercial *Pelargonium* production. During the production of the plants, day temperatures averaged 16° C., night temperatures averaged 14° C. and light levels ranged from 15 kilolux to 100 kilolux. Plants were pinched six weeks after planting and were four months old when the photograph was taken and nine months old when the detailed description was taken. In the detailed description, color references are made to The Royal Horticultural Society Colour Chart, 1995 Edition, except where general terms of ordinary dictionary significance are used.

Botanical classification: *Pelargonium crispum* 'Pacbluebe'.

Parentage:

*Female, or seed, parent*.—Unnamed proprietary selection of *Pelargonium crispum*, not patented.

*Male or pollen parent*.—Unnamed proprietary selection of *Pelargonium crispum*, not patented.

Propagation:

*Type*.—By vegetative terminal cuttings.

*Time to initiate roots, summer and winter*.—About three weeks at temperatures of 20° C.

*Time to produce a rooted young plant, summer*.—About four weeks at temperatures of 20° C.

*Time to produce a rooted young plant, winter*.—About four weeks at temperatures of 18° C.

*Root description*.—Fine, fibrous; white in color.

*Rooting habit*.—Freely branching; dense.

Plant description:

*Plant and growth habit*.—Upright and uniformly rounded plant habit; broad inverted triangle; densely foliated; moderately vigorous growth habit; freely basal branching habit with numerous lateral branches developing per plant.

*Plant height, to top of umbels*.—About 25 cm.

*Plant height, to top of foliar plane*.—About 20 cm.

*Plant width*.—About 30 cm.

*Lateral branches*.—Length: About 5 cm to 15 cm. Diameter: About 2 cm. Internode length: About 2 cm. Texture: Slightly pubescent. Color: Close to 146B.

Leaf description:

*Arrangement*.—Alternate or opposite; simple.

*Length*.—About 2 cm.

*Width*.—About 3 cm.

*Shape*.—Roughly orbicular; palmately lobed.

*Apex*.—Acute.

*Base*.—Cordate, open.

*Margin*.—Biserrate.

*Venation pattern*.—Palmate.

*Texture, upper surface*.—Rough, glabrous.

*Texture, lower surface*.—Slightly pubescent along veins.

*Color*.—Developing and fully expanded leaves, upper surface: Close to 137A; venation, close to 137A. Developing and fully expanded leaves, lower surface: Close to 147B; venation, close to 147B. Zonation pattern: Not observed.

*Petioles*.—Length: About 2 cm. Diameter: About 1 mm. Texture, upper and lower surfaces: Smooth, glabrous. Color, upper and lower surfaces: Close to 143A.

Flower description:

*Flower arrangement and flowering habit*.—Single flowers arranged in inversely conical umbels arising from apical leaf axils; umbels displayed above the foliar plane on strong flexible peduncles; flowers face upright to outward; freely flowering habit; about three to four flowers per umbel with about 40 umbels developing per plant.

*Fragrance*.—None detected.

*Flowering season*.—Early flowering habit, plants begin flowering about four months after planting; in the garden in Germany, flowering begins in April and continues until frost; plants do not require a cooling treatment for flower initiation and development.

*Flower longevity*.—Flowers last about two weeks on the plant; flowers not persistent.

*Umbel height*.—About 3.5 cm.

*Umbel diameter*.—About 6 cm.

*Flower diameter*.—About 2.5 cm to 3 cm.

*Flower depth* (*height*).—About 1.5 cm.

*Flower buds*.—Length: About 1 cm. Diameter: About 4 mm. Shape: Spindle-shaped. Color: Close to 144A.

*Petals*.—Quantity per flower: Five arranged in a single whorl; two upper and three lower petals; petals imbricate. Length, upper petals: About 2.2 cm. Length, lower petals: About 2 cm. Width, upper petals: About 1.7 cm. Width, lower petals: About 1.5 cm. Shape, upper petals: Obovate. Shape, lower petals: Irregularly lobed. Apex, all petals: Rounded; reflexing. Base, all petals: Cuneate. Margin, all petals: Entire. Texture, all petals, upper and lower surfaces: Smooth, glabrous; velvety. Color, all petals: When opening and fully opened, upper surface: Close to 187A; towards the margins and base, close to 75A; venation, close to 59A. When opening and fully opened, lower surface: Close to 187B; towards the margins and base, close to 75A; venation, close to 59A.

*Sepals*.—Quantity per flower: Five arranged in a single whorl. Length: About 1.1 cm. Width: About 3 mm to 5 mm. Shape: Lanceolate. Apex: Acute; reflexing. Margin: Entire. Texture, upper and lower surfaces: Slightly pubescent. Color, upper and lower surfaces: Close to 146C.

*Peduncles* (*umbel stems*).—Length: About 6 cm. Diameter: About 2 mm. Strength: Strong, flexible. Angle: Slightly outwardly slanted. Texture: Sparsely pubescent. Color: Close to 146B.

*Pedicels* (*individual flower stems*).—Length: About 1.5 cm. Diameter: About 1 mm. Strength: Strong; flexible. Texture: Sparsely pubescent. Color: Close to 146B and 166A.

*Reproductive organs*.—Androecium: Stamen quantity per flower: About seven. Anther length: About 2 mm. Anther shape: Tubular. Anther color: Close to 179A. Pollen amount: Abundant. Pollen color: Close to 167A. Gynoecium: Pistil quantity per flower: One. Pistil length: About 1.3 cm. Stigma shape: Five-parted. Stigma color: Close to 59A. Style length: About 8 mm. Style color: Close to 59A. Ovary color: Close to 147C. Seeds and fruits: Seed and fruit development have not been observed on plants of the new *Pelargonium*.

Disease & pest resistance: Plants of the new *Pelargonium* have not been observed to be resistant to pathogens and pests common to *Pelargoniums*.

Temperature tolerance: Plants of the new *Pelargonium* have been observed to tolerate temperatures ranging from about 1° C. to about 35° C. to 40° C.

It is claimed:

1. A new and distinct *Pelargonium* plant named 'Pacbluebe' as illustrated and described.

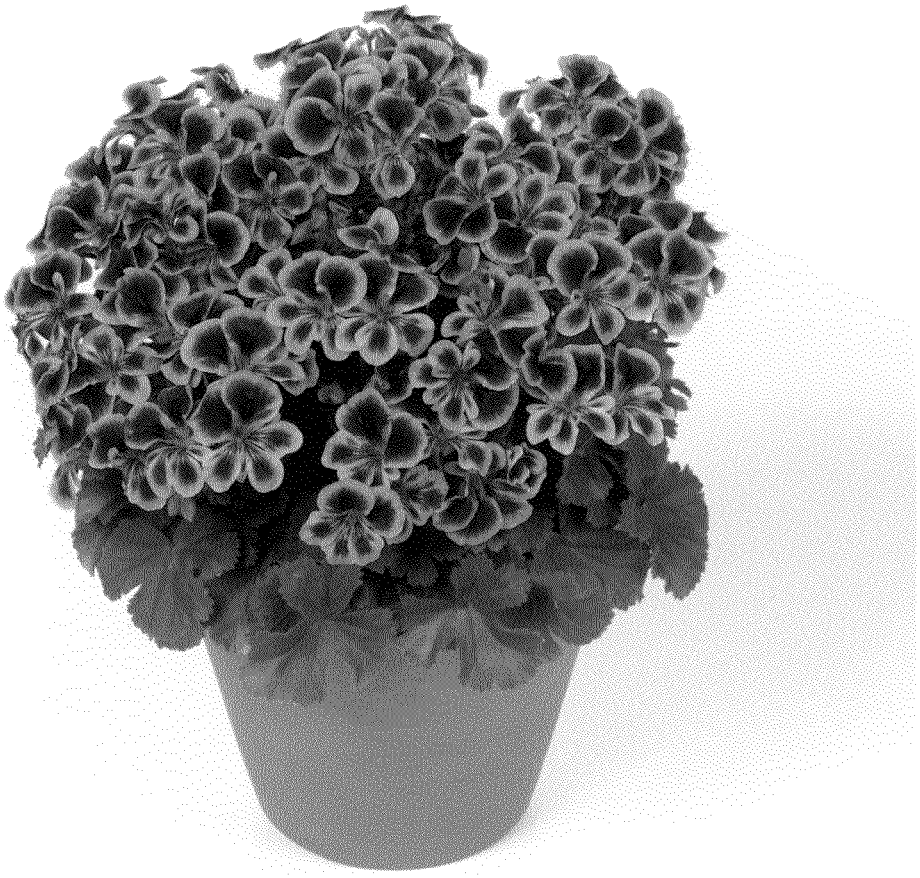

* * * * *